United States Patent
Courtney

(10) Patent No.: US 10,130,056 B2
(45) Date of Patent: Nov. 20, 2018

(54) *BRASSICA NAPUS* L. VAR. *PABULARIA* (DC.) NAMED KX-1

(71) Applicant: Shamrock Seed Company, Inc., Salinas, CA (US)

(72) Inventor: Michael Courtney, New Orleans, LA (US)

(73) Assignee: Shamrock Seed Company, Inc., Salinas, CA (US)

( * ) Notice: Subject to any disclaimer, the term of this patent is extended or adjusted under 35 U.S.C. 154(b) by 103 days.

(21) Appl. No.: 15/426,428

(22) Filed: Feb. 7, 2017

(65) Prior Publication Data

US 2017/0258028 A1    Sep. 14, 2017

Related U.S. Application Data

(60) Provisional application No. 62/306,179, filed on Mar. 10, 2016.

(51) Int. Cl.
*A01H 5/10* (2018.01)

(52) U.S. Cl.
CPC ..................................... *A01H 5/10* (2013.01)

(58) Field of Classification Search
None
See application file for complete search history.

(56) References Cited

U.S. PATENT DOCUMENTS

2017/0071147 A1*  3/2017  Yagoshi .................. A01H 5/10

\* cited by examiner

*Primary Examiner* — Elizabeth McElwain
(74) *Attorney, Agent, or Firm* — Cooley LLP

(57) ABSTRACT

Novel *Brassica napus* L. var. pabularia (DC.), such as *Brassica napus* L. var. pabularia (DC.) designated KX-1 is disclosed. In some embodiments, the invention relates to the seeds of *Brassica napus* L. var. pabularia (DC.) KX-1, to the plants and plant parts of *Brassica napus* L. var. pabularia (DC.) KX-1, and to methods for producing a *Brassica napus* L. var. pabularia (DC.) plant by crossing the *Brassica napus* L. var. pabularia (DC.) KX-1 with itself or another *Brassica napus* L. var. pabularia (DC.) plant. The invention further relates to methods for producing other *Brassica napus* L. var. pabularia (DC.) plants derived from the *Brassica napus* L. var. pabularia (DC.) KX-1.

23 Claims, No Drawings

BRASSICA NAPUS L. VAR. PABULARIA (DC.) NAMED KX-1

CROSS-REFERENCE TO RELATED APPLICATIONS

The present application claims priority to, and the benefit of U.S. Provisional Application Ser. No. 62/306,179, filed on Mar. 10, 2017, which is herein incorporated by reference in its entirety.

FIELD OF THE INVENTION

The present invention relates to the field of agriculture, to new and distinctive *Brassica napus* L. var. pabularia (DC.) cultivar designated KX-1, and to methods of making and using such plant.

BACKGROUND OF THE INVENTION

The following description includes information that may be useful in understanding the present invention. It is not an admission that any of the information provided herein is prior art or relevant to the presently claimed inventions, or that any publication specifically or implicitly referenced is prior art.

*Brassica napus* L. var. pabularia (DC.), also known as Siberian kale is an important and valuable vegetable crop. Thus, a continuing goal of plant breeders is to develop stable, high yielding *Brassica napus* L. var. pabularia (DC.) cultivars that are agronomically sound or unique. The reasons for this goal are to maximize the amount of yield produced on the land used as well as to improve the plant agronomic qualities. To accomplish this goal, the *Brassica napus* L. var. pabularia (DC.) breeder must select and develop *Brassica napus* L. var. pabularia (DC.) plants that have the traits that result in superior cultivars.

SUMMARY OF THE INVENTION

The following embodiments and aspects thereof are described in conjunction with systems, tools and methods which are meant to be exemplary, not limiting in scope.

In various embodiments, one or more of the above-described problems have been reduced or eliminated, while other embodiments are directed to other improvements.

According to the invention, in some embodiments, there is provided a novel *Brassica napus* L. var. pabularia (DC.) cultivar, designated KX-1. This invention thus relates to the seeds of *Brassica napus* L. var. pabularia (DC.) cultivar designated KX-1, to the plants or parts thereof of *Brassica napus* L. var. pabularia (DC.) cultivar designated KX-1, to plants or parts thereof consisting essentially of the phenotypic and morphological characteristics of *Brassica napus* L. var. pabularia (DC.) cultivar designated KX-1, and/or having all the physiological and morphological characteristics of *Brassica napus* L. var. pabularia (DC.) cultivar designated KX-1 and/or having one or more or all of the characteristics of *Brassica napus* L. var. pabularia (DC.) cultivar designated KX-1 listed in Table 1 including, but not limited to, as determined at the 5% significance level when grown in the same environmental conditions, and/or having one or more of the physiological and morphological characteristics of *Brassica napus* L. var. pabularia (DC.) cultivar designated KX-1 listed in Table 1 including, but not limited to, as determined at the 5% significance level when grown in the same environmental conditions, and/or having all the physiological and morphological characteristics of *Brassica napus* L. var. pabularia (DC.) cultivar designated KX-1 listed in Table 1 including but not limited to as determined at the 5% significance level when grown in the same environmental conditions and/or having all the physiological and morphological characteristics of *Brassica napus* L. var. pabularia (DC.) cultivar designated KX-1 listed in Table 1 when grown in the same environmental conditions. The invention also relates to variants, mutants and trivial modifications of the seed or plant of *Brassica napus* L. var. pabularia (DC.) cultivar designated KX-1.

Plant parts of the *Brassica napus* L. var. pabularia (DC.) cultivar of the present invention are also provided, such as a leaf, flower, cell, pollen or ovule obtained from the plant cultivar. The present invention provides leaves of the *Brassica napus* L. var. pabularia (DC.) cultivar of the present invention. Such leaves could be used as fresh products for consumption or in processes resulting in processed products such as food products comprising one or more harvested part of the *Brassica napus* L. var. pabularia (DC.) plant KX-1, for example harvested leaves. The harvested part or food product can be or can comprise the *Brassica napus* L. var. pabularia (DC.) leaves of the *Brassica napus* L. var. pabularia (DC.) plant KX-1 or a salad mixture comprising leaves of the *Brassica napus* L. var. pabularia (DC.) plant KX-1. The food products might have undergone one or more processing steps such as, but not limited to cutting, washing, mixing, etc. All such products are part of the present invention.

The plants and seeds of the present invention include those that may be of an essentially derived variety as defined in section 41(3) of the Plant Variety Protection Act of the United States of America, i.e., a variety that is predominantly derived from *Brassica napus* L. var. pabularia (DC.) cultivar designated KX-1 or from a variety that i) is predominantly derived from *Brassica napus* L. var. pabularia (DC.) cultivar designated KX-1, while retaining the expression of the essential characteristics that result from the genotype or combination of genotypes of *Brassica napus* L. var. pabularia (DC.) cultivar designated KX-1; ii) is clearly distinguishable from *Brassica napus* L. var. pabularia (DC.) cultivar designated KX-1; and iii) except for differences that result from the act of derivation, conforms to the initial variety in the expression of the essential characteristics that result from the genotype or combination of genotypes of the initial variety or cultivar.

In another aspect, the present invention provides regenerable cells. In some embodiments, the regenerable cells are for use in tissue culture of *Brassica napus* L. var. pabularia (DC.) cultivar designated KX-1. In some embodiments, the tissue culture is capable of regenerating plants consisting essentially of the phenotypic and morphological characteristics of *Brassica napus* L. var. pabularia (DC.) cultivar designated KX-1, and/or having all the phenotypic and morphological characteristics of *Brassica napus* L. var. pabularia (DC.) cultivar designated KX-1, and/or having the physiological and morphological characteristics of *Brassica napus* L. var. pabularia (DC.) cultivar designated KX-1, and/or having the characteristics of *Brassica napus* L. var. pabularia (DC.) cultivar designated KX-1. In one embodiment, the regenerated plants have the characteristics of *Brassica napus* L. var. pabularia (DC.) cultivar designated KX-1 listed in Table 1 including but not limited to as determined at the 5% significance level when grown in the same environmental conditions. In some embodiments, the plant parts and cells used to produce such tissue cultures can be embryos, meristematic cells, seeds, callus, pollen, leaves, anthers, pistils, roots, root tips, stems, petioles, cotyledons, hypocotyls, ovaries, seed coat, fruits, endosperm, flowers, axillary buds or the like. Protoplasts produced from such tissue culture are also included in the present invention. The *Brassica napus* L. var. pabularia (DC.) shoots, roots and whole plants regenerated from the tissue culture, as well as the leaves produced by said regenerated plants are also part of the invention. In some embodiments, the whole plants regenerated from the tissue culture have one, more than one, or all of the physiological and morphological characteristics of *Brassica napus* L. var. pabularia (DC.) cultivar designated KX-1 listed in Table 1 including but not limited to when grown in the same environmental conditions.

The invention also discloses methods for vegetatively propagating a plant of the present invention. In some embodiments, the methods comprise collecting a part of a *Brassica napus* L. var. pabularia (DC.) cultivar designated KX-1 and regenerating a plant from said part. In some embodiments, the part can be for example a leaf cutting that is rooted into an appropriate medium according to techniques known by the one skilled in the art. Plants and plant parts thereof such as leaves produced by such methods are also included in the present invention. In another aspect, the plants thereof produced by such methods consist essentially of the phenotypic and morphological characteristics of *Brassica napus* L. var. pabularia (DC.) cultivar designated KX-1, and/or having all the phenotypic and morphological characteristics of *Brassica napus* L. var. pabularia (DC.) cultivar designated KX-1, and/or having the physiological and morphological characteristics of *Brassica napus* L. var. pabularia (DC.) cultivar designated KX-1, and/or having the characteristics of *Brassica napus* L. var. pabularia (DC.) cultivar designated KX-1. In some embodiments, plants produced by such methods consist of one, more than one, or all phenotypic and morphological characteristics of *Brassica napus* L. var. pabularia (DC.) cultivar designated KX-1 listed in Table 1 including but not limited to as determined at the 5% significance level when grown in the same environmental conditions.

Further included in the invention are methods for producing leaves from the *Brassica napus* L. var. pabularia (DC.) cultivar designated KX-1. In some embodiments, the methods comprise growing a *Brassica napus* L. var. pabularia (DC.) cultivar designated KX-1 to produce a *Brassica napus* L. var. pabularia (DC.) leaf. In some embodiments, the methods further comprise harvesting the *Brassica napus* L. var. pabularia (DC.) leaf. In some embodiments, the methods further comprise harvesting the *Brassica napus* L. var. pabularia (DC.) leaf at an early stage of production, leading to "baby leaf" harvest. Such *Brassica napus* L. var. pabularia (DC.) leaves, at any stage of production, are part of the present invention.

Also included in this invention are methods for producing a *Brassica napus* L. var. pabularia (DC.) plant. In some embodiments, the *Brassica napus* L. var. pabularia (DC.) plant is produced by crossing the *Brassica napus* L. var. pabularia (DC.) cultivar designated KX-1 with itself or another plant. In some embodiments, the other plant can be a *Brassica napus* L. var. pabularia (DC.) plant. In some embodiments, the other plant can be a *Brassica napus* L. var. pabularia (DC.) hybrid or line. When crossed with itself, i.e. when KX-1 is crossed with another *Brassica napus* L. var. pabularia (DC.) cultivar KX-1 or self-pollinated, *Brassica napus* L. var. pabularia (DC.) cultivar KX-1 will be conserved (e.g. as an inbred). When crossed with another, different *Brassica napus* L. var. pabularia (DC.) plant, an F1 hybrid seed is produced if the different *Brassica napus* L. var. pabularia (DC.) plant is an inbred and a "three-way cross" seed is produced if the different *Brassica napus* L. var. pabularia (DC.) plant is a hybrid. Such F1 hybrid seed and three-way hybrid seeds and plants produced by growing said F1 and three-way hybrid seeds are included in the present invention. Methods for producing an F1 and three-way hybrid *Brassica napus* L. var. pabularia (DC.) seed comprising crossing *Brassica napus* L. var. pabularia (DC.) cultivar KX-1 plant with a different *Brassica napus* L. var. pabularia (DC.) line or hybrid and harvesting the resultant hybrid *Brassica napus* L. var. pabularia (DC.) seed are also part of the invention. The hybrid *Brassica napus* L. var. pabularia (DC.) seeds produced by the methods comprising crossing *Brassica napus* L. var. pabularia (DC.) cultivar KX-1 plant with a different *Brassica napus* L. var. pabularia (DC.) plant and harvesting the resultant hybrid *Brassica napus* L. var. pabularia (DC.) seed are included in the invention, as are included the hybrid *Brassica napus* L. var. pabularia (DC.) plants or parts thereof and seeds produced by said grown hybrid *Brassica napus* L. var. pabularia (DC.) plants.

Also included in this invention are methods for producing a hybrid *Brassica* plant. In some embodiments, the hybrid *Brassica* plant is produced by crossing the *Brassica napus* L. var. pabularia (DC.) cultivar designated KX-1 with another plant. In some embodiments, the other plant can be a variety of the *Brassica* plant species selected from the group consisting of *Brassica napus* (e.g., rutabaga, Siberian kale), *Brassica rapa* (e.g., Chinese cabbage, pai-tsai, mizuna, Chinese mustard, broccoli raab, and turnip), *Brassica oleracea* (e.g., cabbage, broccoli, cauliflower, Brussels sprouts, kohlrabi, collards, kale), *Raphanus sativus* (e.g., radish), *Brassica nigra* (e.g., black mustard), *Brassica carinata* (e.g., Ethiopian mustard), *Brassica juncea* (e.g., brown or Indian mustard), and *Armoracea rusticana* (e.g., horseradish). When crossed with another, different *Brassica* plant, an F1 hybrid seed is produced if the different *Brassica* plant is an inbred and a "three-way cross" seed is produced if the different *Brassica* plant is a hybrid. Such F1 hybrid seed and three-way hybrid seeds and plants produced by growing said F1 and three-way hybrid seeds are included in the present invention. Methods for producing an F1 and three-way hybrid *Brassica* seed comprising crossing *Brassica napus* L. var. pabularia (DC.) cultivar KX-1 plant with a different *Brassica* line or hybrid and harvesting the resultant hybrid *Brassica* seed are also part of the invention. The hybrid *Brassica* seeds produced by the methods comprising crossing *Brassica napus* L. var. pabularia (DC.) cultivar KX-1 plant with a different *Brassica* plant and harvesting the resultant hybrid *Brassica* seed are included in the invention, as are included the hybrid plants or parts thereof and seeds produced by said grown hybrid *Brassica* plants.

Further included in the invention are methods for producing a *Brassica napus* L. var. pabularia (DC.) seed and plants made thereof. In some embodiments, said methods comprise self-pollinating the *Brassica napus* L. var. pabularia (DC.) cultivar KX-1 and harvesting the resultant seeds. *Brassica napus* L. var. pabularia (DC.) seeds produced by such method are also part of the invention.

In another embodiment, this invention also relates to methods for producing other *Brassica napus* L. var. pabularia (DC.) plants derived from *Brassica napus* L. var. pabularia (DC.) cultivar KX-1 and to the *Brassica napus* L. var. pabularia (DC.) plants derived by the use of those methods.

In some embodiments, such methods for producing a *Brassica napus* L. var. pabularia (DC.) plant derived from the *Brassica napus* L. var. pabularia (DC.) cultivar KX-1 comprise (a) self-pollinating the *Brassica napus* L. var. pabularia (DC.) cultivar KX-1 plant at least once to produce a progeny plant derived from *Brassica napus* L. var. pabularia (DC.) cultivar KX-1. In some embodiments, the methods further comprise (b) crossing the progeny plant derived from *Brassica napus* L. var. pabularia (DC.) cultivar KX-1 with itself or a second *Brassica napus* L. var. pabularia (DC.) plant to produce a seed of a progeny plant of a subsequent generation. In some embodiments, the methods further comprise (c) growing the progeny plant of the subsequent generation. In some embodiments, the method further comprises (d) crossing the progeny plant of the subsequent generation with itself or a second *Brassica napus* L. var. pabularia (DC.) plant to produce a *Brassica napus* L. var. pabularia (DC.) plant further derived from the *Brassica napus* L. var. pabularia (DC.) cultivar KX-1. In further embodiments, step (b), step (c) and/or step (d) are repeated for at least 1, 2, 3, 4, 5, 6, 7, 8, or more generations to produce a *Brassica napus* L. var. pabularia (DC.) plant derived from the *Brassica napus* L. var. pabularia (DC.) cultivar KX-1. In some embodiments, within each crossing cycle, the second plant is the same plant as the second plant in the last crossing cycle. In some embodiment, within each crossing cycle, the second plant is different from the second plant of the last crossing cycle.

Another method for producing a *Brassica napus* L. var. pabularia (DC.) plant derived from the variety KX-1, comprises the steps of: (a) crossing the KX-1 plant with a second *Brassica napus* L. var. pabularia (DC.) plant to produce a progeny plant derived from *Brassica napus* L. var. pabularia (DC.) cultivar KX-1. In some embodiments, the method further comprises (b) crossing the progeny plant derived from *Brassica napus* L. var. pabularia (DC.) cultivar KX-1 with itself or a second *Brassica napus* L. var. pabularia (DC.) plant to produce a seed of a progeny plant of a subsequent generation. In some embodiments, the method further comprises (c) growing the progeny plant of the subsequent generation from the seed; In some embodiments, the method further comprises (d) crossing the progeny plant of the subsequent generation with itself or a different *Brassica napus* L. var. pabularia (DC.) plant to produce a *Brassica napus* L. var. pabularia (DC.) plant derived from KX-1. In a further embodiment, step (b), step (c) and/or step (d) are repeated for at least 1, 2, 3, 4, 5, 6, 7, 8, or more generations to produce a *Brassica napus* L. var. pabularia (DC.) plant derived from KX-1. In some embodiments, within each crossing cycle, the second plant is the same plant as the second plant in the last crossing cycle. In some embodiments, within each crossing cycle, the second plant is different from the second plant in the last crossing cycle.

In another aspect, the present invention provides methods of introducing or modifying one or more desired trait(s) into the *Brassica napus* L. var. pabularia (DC.) cultivar KX-1 and plants or seeds obtained from such methods. The desired trait(s) may be, but not exclusively, a single gene. In some embodiments, the gene is a dominant allele. In some embodiments, the gene is a partially dominant allele. In some embodiments, the gene is a recessive allele. In some embodiments, the gene or genes will confer such traits as male sterility, herbicide resistance, insect resistance, resistance for bacterial, fungal, mycoplasma or viral disease, improved shelf life, water-stress tolerance, delayed senescence or controlled ripening, enhanced plant quality such as improved drought or salt tolerance, enhanced plant vigor, improved or changed colors or improved fresh cut application. For the present invention and the skilled artisan, disease is understood to include, but not limited to fungal diseases, viral diseases, bacterial diseases, mycoplasma diseases, or other plant pathogenic diseases and a disease resistant plant will encompass a plant resistant to fungal, viral, bacterial, mycoplasma, and other plant pathogens. The gene or genes may be naturally occurring *Brassica napus* L. var. pabularia (DC.) gene(s), mutant(s) or genes modified through New Breeding Techniques. In some embodiments, the method for introducing the desired trait(s) is a back-crossing process making use of a series of backcrosses to *Brassica napus* L. var. pabularia (DC.) cultivar KX-1 during which the desired trait(s) is maintained by selection. The single gene conversion plants that can be obtained by the method are included in the present invention. In some embodiments, the desired trait is a transgene.

When dealing with a gene that has been modified, for example through New Breeding Techniques, the trait (genetic modification) could be directly modified into the newly developed line/cultivar such as *Brassica napus* L. var. pabularia (DC.) cultivarKX-1. Alternatively, if the trait is not modified into each newly developed line/cultivar such as lettuce cultivar KX-1, another typical method used by breeders of ordinary skill in the art to incorporate the modified gene is to take a plant already carrying the gene and to use such plant as a donor line to transfer the gene into the newly developed line.

The same would apply for a naturally occurring trait or one arising from spontaneous or induced mutations.

In some embodiments, the backcross breeding process of *Brassica napus* L. var. pabularia (DC.) cultivar KX-1 comprises (a) crossing *Brassica napus* L. var. pabularia (DC.) cultivar KX-1 with plants that comprise the desired trait(s) to produce F1 progeny plants. In some embodiments, the process further comprises (b) selecting the F 1 progeny plants that have the desired trait(s). In some embodiments, the process further comprises (c) crossing the selected F1 progeny plants with the *Brassica napus* L. var. pabularia (DC.) cultivar KX-1 plants to produce backcross progeny plants. In some embodiments, the process further comprises (d) selecting for backcross progeny plants that have the desired trait(s) and physiological and morphological characteristics of the *Brassica napus* L. var. pabularia (DC.) cultivar KX-1 to produce selected backcross progeny plants. In some embodiments, the process further comprises (e) repeating steps (c) and (d) one, two, three, four, five six, seven, eight, nine or more times in succession to produce selected, second, third, fourth, fifth, sixth, seventh, eighth, ninth or higher backcross progeny plants that have the desired trait(s) and consist essentially of the phenotypic and morphological characteristics of the *Brassica napus* L. var. pabularia (DC.) cultivar KX-1, and/or have all the phenotypic and morphological characteristics of the *Brassica napus* L. var. pabularia (DC.) cultivar KX-1, and/or have the desired trait(s) and the physiological and morphological characteristics of the *Brassica napus* L. var. pabularia (DC.) cultivar KX-1 as determined in Table 1, including but not limited to when grown in the same environmental conditions or including but not limited to at a 5% significance level when grown in the same environmental conditions. In some embodiments, the backcross breeding process of *Brassica napus* L. var. pabularia (DC.) cultivar of KX-1 comprises the following steps: (a) crossing *Brassica napus* L. var. pabularia (DC.) cultivar KX-1 with plants of another line that comprise the desired trait(s) to produce F 1 progeny plants, (b) selecting the F 1 progeny plants that have the desired trait(s); (c) crossing the selected F1 progeny plants with the *Brassica napus* L. var. pabularia (DC.) cultivar KX-1 plants to produce backcross progeny plants; (d) selecting for backcross progeny plants that have the desired trait(s) and physiological and morphological characteristics of the *Brassica napus* L. var. pabularia (DC.) cultivar KX-1 to produce selected backcross progeny plants; and (e) repeating steps (c) and (d) one, two, three, four, five six, seven, eight, nine or more times in succession to produce selected, second, third, fourth, fifth, sixth, seventh, eighth, ninth or higher backcross progeny plants that consist essentially of the phenotypic and morphological characteristics of the *Brassica napus* L. var. pabularia (DC.) cultivar KX-1, and/or have all the phenotypic and morphological characteristics of the *Brassica napus* L. var. pabularia (DC.) cultivar KX-1, and/or have the desired trait(s) and the physiological and morphological characteristics of the *Brassica napus* L. var. pabularia (DC.) cultivar KX-1 as determined in Table 1, including but not limited to at a 5% significance level when grown in the same environmental conditions. The *Brassica napus* L. var. pabularia (DC.) plants or seed produced by the methods are also part of the invention. Backcrossing breeding methods, well known to one skilled in the art of plant breeding will be further developed in subsequent parts of the specification.

In an embodiment of this invention is a method of making a backcross conversion of *Brassica napus* L. var. pabularia (DC.) cultivar KX-1. In some embodiments, the method comprises crossing *Brassica napus* L. var. pabularia (DC.) cultivar KX-1 with a donor plant comprising a mutant gene(s), a naturally occurring gene(s) or a gene(s) and/or sequences modified through the use of New Breeding Techniques conferring one or more desired trait to produce F1 progeny plant. In some embodiment, the method further comprises selecting the F1 progeny plant comprising the naturally occurring gene(s), mutant gene(s) or modified gene(s) and/or sequences conferring the one or more desired trait. In some embodiments, the method further comprises backcrossing the selected progeny plant to the *Brassica napus* L. var. pabularia (DC.) cultivar KX-1. This method may further comprise the step of obtaining a molecular marker profile of the *Brassica napus* L. var. pabularia (DC.) cultivar KX-1 and using the molecular marker profile to select for the progeny plant with the desired trait and the molecular marker profile of the *Brassica napus* L. var. pabularia (DC.) cultivar KX-1. The plants or parts thereof produced by such methods are also part of the present invention.

In some embodiments of the invention, the number of loci that may be backcrossed into the *Brassica napus* L. var. pabularia (DC.) cultivar KX-1 is at least 1, 2, 3, 4, 5 or more. A single locus may contain one or several genes. A single locus conversion also allows for making one or more site specific changes to the plant genome, such as, without limitation, one or more nucleotide change, deletion, insertions, etc. In some embodiments, the single locus conversion is performed by genome editing, a.k.a. genome editing with engineered nucleases (GEEN). In some embodiments, the genome editing comprises using one or more engineered nucleases. In some embodiments, the engineered nucleases include, but are not limited to Zinc finger nucleases (ZFNs), Transcription Activator-Like Effector Nucleases (TALENs), the CRISPR/Cas system, engineered meganuclease re-engineered homing endonucleases, and endonucleases for DNA guided genome editing (Gao et al., Nature Biotechnology (2016), doi: 10.1038/nbt.3547). In some embodiments, the single locus conversion changes one or several nucleotides of the plant genome. Such genome editing techniques are some of the techniques now known by a person skilled in the art and herein are collectively referred to as 'New Breeding Techniques'.

The invention further provides methods for developing *Brassica napus* L. var. pabularia (DC.) plants in a *Brassica napus* L. var. pabularia (DC.) plant breeding program using plant breeding techniques including but not limited to, recurrent selection, backcrossing, pedigree breeding, genomic selection, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, Single Nucleotide Polymorphisms (SNPs), etc.) enhanced selection, genetic marker enhanced selection and transformation. Seeds, *Brassica napus* L. var. pabularia (DC.) plants, and parts thereof produced by such breeding methods are also part of the invention.

The invention also relates to variants, mutants and trivial modifications of the seed or plant of the *Brassica napus* L. var. pabularia (DC.) cultivar KX-1. Variants, mutants and trivial modifications of the seed or plant of *Brassica napus* L. var. pabularia (DC.) cultivar KX-1 can be generated by methods available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense RNA interference and other techniques such as the New Breeding Techniques. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entity).

The invention also relates to a mutagenized population of the *Brassica napus* L. var. pabularia (DC.) cultivar KX-1 and methods of using such populations. In some embodiments, the mutagenized population can be used in screening for new *Brassica napus* L. var. pabularia (DC.) plants which comprises one or more or all of the morphological and physiological characteristics of *Brassica napus* L. var. pabularia (DC.) cultivar KX-1. In some embodiments, the new *Brassica napus* L. var. pabularia (DC.) plants obtained from the screening process comprise all of the morphological and physiological characteristics of the *Brassica napus* L. var. pabularia (DC.) cultivar KX-1, and one or more additional or different morphological and physiological characteristics that *Brassica napus* L. var. pabularia (DC.) cultivar KX-1 does not have.

This invention also is directed to methods for producing a *Brassica napus* L. var. pabularia (DC.) plant by crossing a first parent *Brassica napus* L. var. pabularia (DC.) plant with a second parent *Brassica napus* L. var. pabularia (DC.) plant wherein either the first or second parent *Brassica napus* L. var. pabularia (DC.) plant is a *Brassica napus* L. var. pabularia (DC.) cultivar KX-1. Further, both first and second parent *Brassica napus* L. var. pabularia (DC.) plants can come from the *Brassica napus* L. var. pabularia (DC.) cultivar KX-1. Further, the *Brassica napus* L. var. pabularia (DC.) cultivar KX-1 can be self-pollinated i.e. the pollen of a *Brassica napus* L. var. pabularia (DC.) cultivar KX-1 can pollinate the ovule of the same *Brassica napus* L. var. pabularia (DC.) cultivar KX-1, respectively. When crossed with another *Brassica napus* L. var. pabularia (DC.) plant, a hybrid seed is produced. Such methods of hybridization and self-pollination are well known to those skilled in the art of breeding.

A *Brassica napus* L. var. pabularia (DC.) cultivar such as *Brassica napus* L. var. pabularia (DC.) cultivar KX-1 has been produced through several cycles of self-pollination and is therefore to be considered as a homozygous plant or line. An inbred line can also be produced through the dihaploid system which involves doubling the chromosomes from a haploid plant or embryo thus resulting in an inbred line that is genetically stable (homozygous) and can be reproduced without altering the inbred line: Haploid plants could be obtained from haploid embryos that might be produced from microspores, pollen, anther cultures or ovary cultures or spontaneous haploidy. The haploid embryos may then be doubled by chemical treatments such as by colchicine or be doubled autonomously. The haploid embryos may also be grown into haploid plants and treated to induce the chromosome doubling. In either case, fertile homozygous plants are obtained. A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting F1 hybrid, theoretically in the arrangement and organization created by the plant breeder in the original parental line.

As long as the homozygosity of the parental lines is maintained, the resulting F1 hybrid cross shall be stable. The F1 hybrid is then a combination of phenotypic characteristics issued from two arrangement and organization of genes, both created by a person skilled in the art through the breeding process.

Still further, this invention also is directed to methods for producing a *Brassica napus* L. var. pabularia (DC.) plant derived from *Brassica napus* L. var. pabularia (DC.) plant cultivar KX-1 by crossing *Brassica napus* L. var. pabularia (DC.) cultivar KX-1 with a second *Brassica napus* L. var. pabularia (DC.) plant. In some embodiments, the method further comprises obtaining a progeny seed from the cross. In some embodiment, the method further comprises growing the progeny seed, and possibly repeating the crossing and growing steps with the *Brassica napus* L. var. pabularia (DC.) cultivar KX-1 -derived plant from 0 to 7, or more times. Thus, any such methods using the *Brassica napus* L. var. pabularia (DC.) cultivar KX-1 are part of this invention: selfing, backcrosses, hybrid production, crosses to populations, and the like. All plants produced using *Brassica napus* L. var. pabularia (DC.) cultivar KX-1 as a parent are within the scope of this invention, including plants derived from *Brassica napus* L. var. pabularia (DC.) cultivar KX-1. In some embodiment, such plants have one, more than one, or all phenotypic and morphological characteristics of *Brassica napus* L. var. pabularia (DC.) cultivar KX-1 listed in Table 1 including but not limited to as determined at the 5% significance level when grown in the same environmental conditions.

Such plants might exhibit additional and desired characteristics or traits such as high seed yield, high seed germination, seedling vigor, early maturity, high yield, disease tolerance or resistance, and adaptability for soil and climate conditions. Consumer-driven traits, such as a preference for a given leaf size, shape, color, texture, taste, are other traits that may be incorporated into new *Brassica napus* L. var. pabularia (DC.) plants developed by this invention.

A *Brassica napus* L. var. pabularia (DC.) plant can also be propagated vegetatively. A part of the plant, for example a shoot tissue, is collected, and a new plant is obtained from the part. Such part typically comprises an apical meristem of the plant. The collected part is transferred to a medium allowing development of a plantlet, including for example rooting or development of shoots. This is achieved using methods well-known in the art. Accordingly, in one embodiment, a method of vegetatively propagating a plant of the present invention comprises collecting a part of a plant according to the present invention, e.g. a shoot tissue, and obtaining a plantlet from said part. In one embodiment, a method of vegetatively propagating a plant of the present invention comprises: a) collecting tissue of a plant of the present invention; b) rooting said proliferated shoots to obtain rooted plantlets. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets. In one embodiment, such method further comprises growing a plant from said plantlets. In one embodiment, leaves are harvested from said plant. In one embodiment, the leaves are processed into products prepared cut leaves.

In some embodiments, the present invention teaches a seed of *Brassica napus* L. var. pabularia (DC.) cultivar KX-1, wherein a representative sample of seed of said *Brassica napus* L. var. pabularia (DC.) cultivar is deposited under NCIMB No 42703.

In some embodiments, the present invention teaches a *Brassica napus* L. var. pabularia (DC.) plant, or a part thereof, produced by growing the deposited KX-1 seed.

In some embodiments, the present invention teaches *Brassica napus* L. var. pabularia (DC.) plant parts, wherein the *Brassica napus* L. var. pabularia (DC.) part is selected from the group consisting of: a leaf, a flower, an ovule, pollen, and a cell.

In some embodiments, the present invention teaches a *Brassica napus* L. var. pabularia (DC.) plant, or a part thereof, having all of the characteristics of *Brassica napus* L. var. pabularia (DC.) cultivar KX-1 as listed in Table 1 of this application including but not limited to when grown in the same environmental conditions.

In some embodiments, the present invention teaches a *Brassica napus* L. var. pabularia (DC.) plant, or a part thereof, having all of the physiological and morphological characteristics of *Brassica napus* L. var. pabularia (DC.) cultivar KX-1, wherein a representative sample of seed of said *Brassica napus* L. var. pabularia (DC.) plant was deposited under NCIMB No 42703.

In some embodiments, the present invention teaches a composition comprising regenerable cells produced from the plant or plant part grown from the deposited *Brassica napus* L. var. pabularia (DC.) cultivar KX-1 seed, or other plant part or plant cell. In some embodiments, the composition comprises a growth media. In some embodiments, the growth media is solid or a synthetic cultivation medium. In some embodiments, the composition is tissue culture of regenerable cells produced from the plant or plant part grown from the deposited *Brassica napus* L. var. pabularia (DC.) cultivar KX-1 seed, wherein cells of the tissue culture are produced from a plant part selected from the group consisting of protoplasts, embryos, meristematic cells, callus, pollen, ovules, flowers, seeds, leaves, roots, root tips, anthers, stems, petioles, head, axillary buds, cotyledons and hypocotyls. In some embodiments, the plant part includes protoplasts produced from a plant grown from the deposited *Brassica napus* L. var. pabularia (DC.) cultivar KX-1 seed.

In some embodiments, the present invention teaches a *Brassica napus* L. var. pabularia (DC.) plant regenerated from the tissue culture from a plant grown from the deposited *Brassica napus* L. var. pabularia (DC.) cultivar KX-1 seed, said plant having the characteristics of *Brassica napus* L. var. pabularia (DC.) cultivar KX-1, wherein a representative sample of seed of said *Brassica napus* L. var. pabularia (DC.) cultivar KX-1 is deposited under NCIMB No 42703.

In some embodiments, the present invention teaches a *Brassica napus* L. var. pabularia (DC.) leaf produced from plants grown from the deposited *Brassica napus* L. var. pabularia (DC.) cultivar KX-1 seed.

In some embodiments, the methods of producing said *Brassica napus* L. var. pabularia (DC.) leaf comprise a) growing the *Brassica napus* L. var. pabularia (DC.) plant from deposited *Brassica napus* L. var. pabularia (DC.) cultivar KX-1 seed to produce a *Brassica napus* L. var. pabularia (DC.) leaf, and b) harvesting said *Brassica napus* L. var. pabularia (DC.) leaf. In some embodiments, the present invention also teaches a *Brassica napus* L. var. pabularia (DC.) leaf produced by the method of producing *Brassica napus* L. var. pabularia (DC.) leaf as described above.

In some embodiments, the present invention teaches methods for producing a *Brassica napus* L. var. pabularia (DC.) seed comprising crossing a first parent *Brassica napus* L. var. pabularia (DC.) plant with a second parent *Brassica napus* L. var. pabularia (DC.) plant and harvesting the resultant *Brassica napus* L. var. pabularia (DC.) seed, wherein said first parent *Brassica napus* L. var. pabularia (DC.) plant and/or second parent *Brassica napus* L. var. pabularia (DC.) plant is the *Brassica napus* L. var. pabularia (DC.) plant produced from the deposited *Brassica napus* L. var. pabularia (DC.) cultivar KX-1 seed, or a *Brassica napus* L. var. pabularia (DC.) plant having all of the characteristics of *Brassica napus* L. var. pabularia (DC.) cultivar KX-1 as listed in Table 1 of this application, including but not limited to when grown in the same environmental conditions In some embodiments, the present invention teaches methods for producing a *Brassica napus* L. var. pabularia (DC.) seed comprising self-pollinating the *Brassica napus* L. var. pabularia (DC.) plant grown from the deposited *Brassica napus* L. var. pabularia (DC.) cultivar KX-1 seed and harvesting the resultant *Brassica napus* L. var. pabularia (DC.) seed.

In some embodiments, the present invention teaches the seed produced by any of the above described methods.

In some embodiments, the present invention teaches methods of vegetatively propagating the *Brassica napus* L. var. pabularia (DC.) plant grown from the deposited *Brassica napus* L. var. pabularia (DC.) cultivar KX-1 seed, said method comprising a) collecting part of a plant grown from the deposited *Brassica napus* L. var. pabularia (DC.) cultivar KX-1 seed and b) regenerating a plant from said part.

In some embodiments, the method further comprises harvesting a leaf from said vegetatively propagated plant.

In some embodiments, the present invention teaches the plant, the leaves thereof of plants vegetatively propagated from plant parts of plants grown from the deposited *Brassica napus* L. var. pabularia (DC.) cultivar KX-1 seed.

In some embodiments, the present invention teaches methods of producing a *Brassica napus* L. var. pabularia (DC.) plant derived from the *Brassica napus* L. var. pabularia (DC.) cultivar PYTHON. In some embodiments, the methods comprises (a) self-pollinating the plant grown from the deposited *Brassica napus* L. var. pabularia (DC.) cultivar KX-1 seed at least once to produce a progeny plant derived from *Brassica napus* L. var. pabularia (DC.) cultivar KX-1. In some embodiment, the method further comprise (b) crossing the progeny plant derived from *Brassica napus* L. var. pabularia (DC.) cultivar KX-1 with itself or a second *Brassica napus* L. var. pabularia (DC.) plant to produce a seed of a progeny plant of a subsequent generation; and (c) growing the progeny plant of the subsequent generation from the seed, and crossing the progeny plant of the subsequent generation with itself or a second *Brassica napus* L. var. pabularia (DC.) plant to produce a *Brassica napus* L. var. pabularia (DC.) plant derived from the *Brassica napus* L. var. pabularia (DC.) cultivar KX-1. In some embodiments said method further comprises the step of: (d) repeating steps b) and/or c) for at least 1, 2, 3, 4, 5, 6, 7, or more generation to produce a *Brassica napus* L. var. pabularia (DC.) plant derived from the *Brassica napus* L. var. pabularia (DC.) cultivar KX-1.

In some embodiments, the present invention teaches methods of producing a *Brassica napus* L. var. pabularia (DC.) plant derived from the *Brassica napus* L. var. pabularia (DC.) cultivar KX-1, the methods comprising (a) crossing the plant grown from the deposited *Brassica napus* L. var. pabularia (DC.) cultivar KX-1 seed with a second *Brassica napus* L. var. pabularia (DC.) plant to produce a progeny plant derived from *Brassica napus* L. var. pabularia (DC.) cultivar KX-1. In some embodiments, the methods further comprise (b) crossing the progeny plant derived from *Brassica napus* L. var. pabularia (DC.) cultivar KX-1 with itself or a second *Brassica napus* L. var. pabularia (DC.) plant to produce a seed of a progeny plant of a subsequent generation; and (c) growing the progeny plant of the subsequent generation from the seed and crossing the progeny plant of the subsequent generation with itself or a second *Brassica napus* L. var. pabularia (DC.) plant to produce a *Brassica napus* L. var. pabularia (DC.) plant derived from the *Brassica napus* L. var. pabularia (DC.) cultivar KX-1. In some embodiments said method further comprises the step of: (d) repeating steps (b) and/or (c) for at least 1, 2, 3, 4, 5, 6, 7 or more generation to produce a *Brassica napus* L. var. pabularia (DC.) plant derived from the *Brassica napus* L. var. pabularia (DC.) cultivar KX-1.

In some embodiments, the present invention teaches plants grown from the deposited *Brassica napus* L. var. pabularia (DC.) cultivar KX-1 seed wherein said plants comprise a single locus conversion. As used herein, the term "a" or "an" refers to one or more of that entity; for example, "a single locus conversion" refers to one or more single locus conversions or at least one single locus conversion. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements. In some embodiments said single locus conversion confers said plant with a trait selected from the group consisting of male sterility, male fertility, herbicide resistance, insect resistance, disease resistance, water stress tolerance, heat tolerance, delayed senescence, improved ripening control, long shelf life, and improved salt tolerance when compared to a suitable check plant. In some embodiments, the check plant is a *Brassica napus* L. var. pabularia (DC.) cultivar KX-1 plant not having said single locus conversion. In some embodiments, the single locus conversion is an artificially mutated gene or a gene or nucleotide sequence modified through the use of New Breeding Techniques.

In addition to the exemplary aspects and embodiments described above, further aspects and embodiments will become apparent by study of the following descriptions.

DETAILED DESCRIPTION OF THE INVENTION

Definitions

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics of the recurrent parent, except for the characteristics derived from the converted gene.

First water date. The date the seed first receives adequate moisture to germinate. This can and often does equal the planting date Immunity to disease(s) and or insect(s). A *Brassica napus* L. var. pabularia (DC.) plant which is not subject to attack or infection by specific disease(s) and or insect(s) is considered immune.

Intermediate resistance to disease(s) and or insect(s). A *Brassica napus* L. var. pabularia (DC.) plant that restricts the growth and development of specific disease(s) and or insect(s), but may exhibit a greater range of symptoms or damage compared to resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant *Brassica napus* L. var. pabularia (DC.) plants are not immune to the disease(s) and or insect(s).

Maturity (Date). Maturity refers to the stage when plants are of full size or optimum weight, and in marketable form or shape to be of commercial or economic value. In leaf types they range from 50-75 days from time of seeding, depending upon the season of the year. In other baby leaf type, they range from 30 to 45 days after planting. In *Brassica napus* L. var. pabularia (DC.) types, they range from 25 to 40 days from time of seeding.

New Breeding Techniques: New breeding techniques are said of various new technologies developed and/or used to create new characteristics in plants through genetic variation, the aim being targeted mutagenesis, targeted introduction of new genes or gene silencing (RdDM). Examples of such new breeding techniques are targeted sequence changes facilitated thru the use of Zinc finger nuclease (ZFN) technology (ZFN-1, ZFN-2 and ZFN-3, see U.S. Pat. No. 9,145,565, incorporated by reference in its entirety), Oligo-nucleotide directed mutagenesis (ODM), Cisgenesis and intragenesis, RNA-dependent DNA methylation (RdDM, which does not necessarily change nucleotide sequence but can change the biological activity of the sequence), Grafting (on GM rootstock), Reverse breeding, Agro-infiltration (agro-infiltration "sensu stricto", agro-inoculation, floral dip), Transcription Activator-Like Effector Nucleases (TAL-ENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease re-engineered homing endonucleases, DNA guided genome editing (Gao et al., Nature Biotechnology (2016), doi: 10.1038/nbt.3547, incorporated by reference in its entirety), and Synthetic genomics. A complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

Plant adaptability. A plant having good plant adaptability means a plant that will perform well in different growing conditions and seasons.

Plant Cell. As used herein, the term "plant cell" includes plant cells whether isolated, in tissue culture or incorporated in a plant or plant part.

Plant Part. As used herein, the term "plant part" includes plant cells, plant protoplasts, plant cell tissue cultures from which *Brassica napus* L. var. pabularia (DC.) plants can be regenerated, plant calli, plant clumps and plant cells that are intact in plants or parts of plants, such as embryos, pollen, ovules, flowers, seeds, rootstock, scions, stems, roots, anthers, pistils, root tips, leaves, meristematic cells, axillary buds, hypocotyls cotyledons, ovaries, seed coat endosperm and the like. In some embodiments, the plant part at least comprises at least one cell of said plant. In some embodiments, the plant part is further defined as a pollen, a meristem, a cell, or an ovule.

Quantitative Trait Loci (QTL) Quantitative trait loci refer to genetic loci that control to some degree numerically representable traits that are usually continuously distributed.

Regeneration. Regeneration refers to the development of a plant from tissue culture.

Resistance to disease(s) and or insect(s). A *Brassica napus* L. var. pabularia (DC.) plant that restricts highly the growth and development of specific disease(s) and or insect(s) under normal disease(s) and or insect(s) attack pressure when compared to susceptible plants. These *Brassica napus* L. var. pabularia (DC.) plants can exhibit some symptoms or damage under heavy disease(s) and or insect(s) pressure.

RHS. RHS refers to the Royal Horticultural Society of England which publishes an official botanical color chart quantitatively identifying colors according to a defined numbering system. The chart may be purchased from Royal Hort. Society Enterprise Ltd. RHS Garden; Wisley, Woking, Surrey GU236QB, UK.

Single gene converted (conversion). Single gene converted (conversion) plants refer to plants which are developed by a plant breeding technique called backcrossing wherein essentially all of the desired morphological and physiological characteristics of a plant are recovered in addition to the single gene transferred into the plant via the backcrossing technique or via genetic engineering. A single gene converted plant can also be referred to a plant obtained though mutagenesis or through the use of some new breeding techniques, whereas the single gene converted plant has essentially all of the desired morphological and physiological characteristics of the original variety in addition to the single gene or nucleotide sequence muted or engineered through the new breeding techniques.

Susceptible to disease(s) and or insect(s). A *Brassica napus* L. var. pabularia (DC.) plant that is susceptible to disease(s) and or insect(s) is defined as a *Brassica napus* L. var. pabularia (DC.) plant that has the inability to restrict the growth and development of specific disease(s) and or insect (s). Plants that are susceptible will show damage when infected and are more likely to have heavy damage under moderate levels of specific disease(s) and or insect(s).

Tolerance to abiotic stresses. A *Brassica napus* L. var. pabularia (DC.) plant that is tolerant to abiotic stresses has the ability to endure abiotic stress without serious consequences for growth, appearance and yield.

Uniformity. Uniformity, as used herein, describes the similarity between plants or plant characteristics which can be a described by qualitative or quantitative measurements.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

*Brassica napus* L. var. pabularia (DC.) Plants

*Brassica napus* L. var. pabularia (DC.), also known as Siberian kale, is a vegetable which has been grown for many years various places worldwide and which is becoming increasingly popular in the USA with the recent development of the industrial culture of ready-to-eat fresh products, in salad mix, dressing and garnishing in gourmet cuisines. This new trend has lead to the development of baby-leaf products such as the ones from KX-1. Delicate leaves are very attractive and appetizing, excellent for dressing gourmet food. They are grown at high concentration and harvested at very young or "baby leaf" stage, typically 15 to 40 days after planting. The planting is often done on wider 80 to 84 inch beds and often containing up to one million plants per acre.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm.

In *Brassica napus* L. var. pabularia (DC.), these important traits may include heavier texture, improved uniformity, especially of the leaves, stem and hypocotyl, higher seed yield, improved color, resistance to diseases and insects, tolerance to drought and heat, better post-harvest shelf-life of the leaves, better standing ability in the field, and better agronomic quality.

In some embodiments, particularly desirable traits that may be incorporated by this invention are improved resistance to different viral, fungal, and bacterial pathogens. Important diseases include but are not limited to fungi such as *Bremia lactucae, Fusarium oxysporum, Sclerotinia* minor or *sclerotorum, Botrytis cinerea, Rhizictonia solani, Microdochium panattonianum, Verticiulium dahliae, Erysiphe chicocearum* or *Pithium tracheiphilum*, virus, such as LMV (lettuce mosaic virus), TSWV (tomato potted wilt virus), "Big vein" (composed of LBW (lettuce big vein virus) and MILV (miratiori lettuce virus)), TBSV (tomato bushy stunt virus), LNSV (lettuce necrotic stunt virus), TuMV (turnip mosaic virus), CMV (cucumber mosaic virus) or BWYV (beet western yellows virus), bacteria such as *Pseudomonas, Xanthomonas* or *Rhizomonas*. Improved resistance to insect pests is another desirable trait that may be incorporated into new *Brassica napus* L. var. pabularia (DC.) plants developed by this invention. Insect pests affecting the various species of *Brassica napus* L. var. pabularia (DC.) include *Nasonovia ribisnigri, Myzus persicae, Macrosiphum euphorbia, Nematodes pratylenchus* or *meloidogyne*, leafminers: *Liriomyza huidobrensis* or *Pemphigus busarius*.

*Brassica napus* L. var. pabularia (DC.) Breeding

The goal of *Brassica napus* L. var. pabularia (DC.) breeding is to develop new, unique and superior *Brassica napus* L. var. pabularia (DC.) cultivar and hybrids. The breeder initially selects and crosses two or more parental lines, followed by repeated selfing and selection, producing many new genetic combinations. Another method used to develop new, unique and superior *Brassica napus* L. var. pabularia (DC.) cultivar occurs when the breeder selects and crosses two or more parental lines followed by haploid induction and chromosome doubling that result in the development of dihaploid cultivars. The breeder can theoretically generate billions of different genetic combinations via crossing, selfing and mutations and the same is true for the utilization of the dihaploid breeding method.

Each year, the plant breeder selects the germplasm to advance to the next generation. This germplasm is grown under unique and different geographical, climatic and soil conditions, and further selections are then made, during and at the end of the growing season. The cultivars developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting cultivars he develops, except possibly in a very gross and general fashion. This unpredictability results in the expenditure of large research monies to develop superior new *Brassica napus* L. var. pabularia (DC.) cultivars.

The development of commercial *Brassica napus* L. var. pabularia (DC.) cultivar requires the development and selection of *Brassica napus* L. var. pabularia (DC.) plants, the crossing of these plants, and the evaluation of the crosses.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes or through the dihaploid breeding method followed by the selection of desired phenotypes. The new cultivars are evaluated to determine which have commercial potential.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

i Pedigree Selection

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). The dihaploid breeding method could also be used. Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release of new cultivars. Similarly, the development of new cultivars through the dihaploid system requires the selection of the cultivars followed by two to five years of testing in replicated plots.

ii Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

When the term *Brassica napus* L. var. pabularia (DC.) cultivar is used in the context of the present invention, this also includes any *Brassica napus* L. var. pabularia (DC.) cultivar plant where one or more desired trait has been introduced through backcrossing methods, whether such trait is a naturally occurring one, a mutant or a gene or a nucleotide sequence modified by the use of New Breeding Techniques. Backcrossing methods can be used with the present invention to improve or introduce one or more characteristic into the *Brassica napus* L. var. pabularia (DC.) cultivar of the present invention. The term "backcrossing" as used herein refers to the repeated crossing of a hybrid progeny back to the recurrent parent, i.e., backcrossing one, two, three, four, five, six, seven, eight, nine, or more times to the recurrent parent. The parental *Brassica napus* L. var. pabularia (DC.) cultivar plant which contributes the gene or the genes for the desired characteristic is termed the nonrecurrent or donor parent. This terminology refers to the fact that the nonrecurrent parent is used one time in the backcross protocol and therefore does not recur. The parental *Brassica napus* L. var. pabularia (DC.) cultivar to which the gene or genes from the nonrecurrent parent are transferred is known as the recurrent parent as it is used for several rounds in the backcrossing protocol.

In a typical backcross protocol, the original cultivar of interest (recurrent parent) is crossed to a second cultivar (nonrecurrent parent) that carries the gene or genes of interest to be transferred. The resulting progeny from this cross are then crossed again to the recurrent parent and the process is repeated until a *Brassica napus* L. var. pabularia (DC.) plant is obtained wherein all the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self-pollination and growing of population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute one or more trait(s) or characteristic(s) in the original inbred parental line in order to find it then in the hybrid made thereof. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the waxy starch characteristic in corn, require selfing the progeny to determine which plant carry the recessive allele(s).

Many single gene traits have been identified that are not regularly selected for in the development of a new parental inbred of a hybrid lettuce plant according to the invention but that can be improved by backcrossing techniques. These genes are generally inherited through the nucleus.

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc, Principles of Plant Breeding). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a parental line of a hybrid variety with exactly the adaptation, yielding ability and quality characteristics of the recurrent parent but superior to that parent in the particular characteristic(s) for which the improvement program was undertaken. Therefore, this method provides the plant breeder with a high degree of genetic control of his work.

The method is scientifically exact because the morphological and agricultural features of the improved variety could be described in advance and because the same variety could, if it were desired, be bred a second time by retracing the same steps (Briggs, "Breeding wheats resistant to bunt by the backcross method", 1930 Jour. Amer. Soc. Agron., 22: 289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred.

The backcross technique is not only desirable when breeding for disease resistance but also for the adjustment of morphological characters, colour characteristics and simply inherited quantitative characters such as earliness, plant height and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e. grain size. 'Lady Wright', a long grain variety was used as the donor parent and 'Coloro', a short grain one as the recurrent parent. After four backcrosses, the medium grain type variety 'Calady' was produced.

iii Single-Seed Descent and Multiple Seed Procedures

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more flower containing seed from each plant in a population and blend them together to form a bulk seed lot. Part of the bulked seed is used to plant the next generation and part is put in reserve. The procedure has been referred to as modified single-seed descent or the bulk technique.

The multiple-seed procedure has been used to save labor at harvest. It is considerably faster than removing one seed from each flower by hand for the single seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

iii Open-Pollinated Populations

The improvement of open-pollinated populations of such crops as rye, maize and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement.

First, there is the situation in which a population is changed en masse by a chosen selection procedure. The outcome is an improved population that is indefinitely propagable by random-mating within itself in isolation.

Second, the synthetic variety attains the same end result as population improvement, but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

A) Mass Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

B) Synthetics

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or more cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

iv. Hybrids

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the F1 progeny. A double-cross hybrid is produced from four inbred lines crossed in pairs (A×B and C×D) and then the two F1 hybrids are crossed again (A×B)×(C×D). Much of the hybrid vigor and uniformity exhibited by F1 hybrids is lost in the next generation (F2). Consequently, seed from F2 hybrid varieties is not used for planting stock.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

v. Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences*, USA, 99:9828-9832) and Quarrie et al. (Quarrie et al., 1999, *Journal of Experimental Botany*, 50(337): 1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs, SNPs or SSRs). Markers linked to the phenotype can be identified and used for breeding or QTL mapping.

vi. Hand-Pollination Method

Hand pollination describes the crossing of plants via the deliberate fertilization of female ovules with pollen from a desired male parent plant. In some embodiments the donor or recipient female parent and the donor or recipient male parent line are planted in the same field. In some embodiments the donor or recipient female parent and the donor or recipient male parent line are planted in the same greenhouse. The inbred male parent can be planted earlier than the female parent to ensure adequate pollen supply at the pollination time. In some embodiments, the male parent and female parent can be planted at a ratio of 1 male parent to 4-10 female parents. Pollination is started when the female parent flower is ready to be fertilized. Female flower buds that are ready to open in the following days are identified, covered with paper cups or small paper bags that prevent bee or any other insect from visiting the female flowers, and marked with any kind of material that can be easily seen the next morning. The male flowers of the male parent are collected in the early morning before they are open and visited by pollinating insects. The covered female flowers of the female parent, which have opened, are un-covered and pollinated with the collected fresh male flowers of the male parent, starting as soon as the male flower sheds pollen. The pollinated female flowers are again covered after pollination to prevent bees and any other insects visit. The pollinated female flowers are also marked. The marked flowers are harvested. In some embodiments, the male pollen used for fertilization has been previously collected and stored.

vii. Bee-Pollination Method

Using the bee-pollination method, the parent plants are usually planted within close proximity. In some embodiments more female plants are planted to allow for a greater production of seed. Insects are placed in the field or greenhouses for transfer of pollen from the male parent to the female flowers of the female parent.

viii. Targeting Induced Local Lesions in Genomes (TILLING)

Breeding schemes of the present application can include crosses with TILLING® plant cultivars. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING® or the natural mutation or SNP in EcoTILLING), they provoke shape change in the double strand DNA fragment which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus* L. var. pabularia (DC.); John Innes Centre (UK), focusing on *Brassica rapa*; Fred Hutchinson Cancer Research, focusing on Arabidopsis; Southern Illinois University (USA), focusing on Soybean; John Innes Centre (UK), focusing on Lotus and Medicago ; and INRA (France), focusing on Pea and Tomato.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

Thus in some embodiments, the breeding methods of the present disclosure include breeding with one or more TILLING plant lines with one or more identified mutations.

viii Mutation Breeding

Mutation breeding is another method of introducing new variation and subsequent traits into plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co.

New breeding techniques such as the ones involving the uses of Zinc Finger Nucleases or oligonucleotide directed mutagenesis shall also be used to generate genetic variability and introduce new traits into varieties.

ix. Double Haploids and Chromosome Doubling

One way to obtain homozygous plants without the need to cross two parental lines followed by a long selection of the segregating progeny, and/or multiple backcrossings is to produce haploids and then double the chromosomes to form doubled haploids. Haploid plants can occur spontaneously, or may be artificially induced via chemical treatments or by crossing plants with inducer lines (Seymour et al. 2012, PNAS vol 109, pg 4227-4232; Zhang et al., 2008 Plant Cell Rep. Dec 27(12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 pg 63-72; Doubled Haploid Production in Crop Plants 2003 edited by Maluszynski ISBN 1-4020-1544-5). The production of doubled haploid plants yields highly uniform cultivars and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

x. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

xi. Embryo Rescue

Alternatively, embryo rescue may be employed in the transfer of resistance-conferring genomic material from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, *In vitro culture of higher plants*, Springer, ISBN 079235267x, 9780792352679, which is incorporated herein by reference in its entirety).

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection.

In one embodiment, the plants are selected on the basis of one or more phenotypic traits. Skilled persons will readily appreciate that such traits include any observable characteristic of the plant, including for example growth rate, height, weight, color, taste, smell, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (herbage or grain or fiber or oil, or fruit or leaves) or biomass production; effects on plant growth that results in an increased seed yield for a crop; effects on plant growth which result in an increased yield; effects on plant growth that lead to an increased resistance or tolerance to disease including fungal, viral or bacterial diseases, to mycoplasma or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color or taste, for example the color intensity of *Brassica napus* L. var. pabularia (DC.) leaves, or the taste of said leaves.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (transcriptome sequencing), qRTPCR (quantitative real time PCR).

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Fl ow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene or QTL or a desirable trait (e.g., a co-segregating nucleic acid, or other marker).

In another embodiment, the evaluating step comprises immunological detection (e.g., precipitation and agglutination tests, ELISA (e.g., Lateral Fl ow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the mRNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 50° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cation concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel like polyacrylamide gels and ethidium bromide (or other nucleic acid staining).

Conventional RT-PCR is a time-consuming technique with important limitations when compared to real time PCR techniques.. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general nonspecific DNA Binding Dyes such as SYBR Green I, TaqMan Probes and Molecular Beacons (including Scorpions).

The real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

Other forms of nucleic acid detection can include next generation sequencing methods such as DNA SEQ or RNA SEQ using any known sequencing platform including, but not limited to: Roche 454, Solexa Genome Analyzer, AB SOLiD, Illumina GA/HiSeq, Ion PGM, Mi Seq, among others (Liu et al,. 2012 Journal of Biomedicine and Biotechnology Volume 2012 ID 251364; Franca et al., 2002 Quarterly Reviews of Biophysics 35 pg. 169-200; Mardis 2008 Genomics and Human Genetics vol 9 pg 387-402).

In other embodiments, nucleic acids may be detected with other high throughput hybridization technologies including microarrays, gene chips, LNA probes, nanoStrings, and fluorescence polarization detection among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full service analysis tools capable of handling nucleic acid/protein marker extractions, detection, storage and analysis.

Quantitative Trait Loci

Breeding schemes of the present application can include crosses between donor and recipient plants. In some embodiments said donor plants contain a gene or genes of interest which may confer the plant with a desirable phenotype. The recipient line can be an elite line or cultivar having certain favorite traits such for commercial production. In one embodiment, the elite line may contain other genes that also impart said line with the desired phenotype. When crossed together, the donor and recipient plant may create a progeny plant with combined desirable loci which may provide quantitatively additive effect of a particular characteristic. In that case, QTL mapping can be involved to facilitate the breeding process.

A QTL (quantitative trait locus) mapping can be applied to determine the parts of the donor plant's genome conferring the desirable phenotype, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait . Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*, 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and how do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, SNPs, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R.G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, PLoS Biol.;2(10):e245).

Tissue Culture

As it is well known in the art, tissue culture of *Brassica napus* L. var. pabularia (DC.) can be used for the in vitro regeneration of *Brassica napus* L. var. pabularia (DC.) plants. Tissues cultures of various tissues of *Brassica napus* L. var. pabularia (DC.) and regeneration of plants therefrom are well known. Thus, another aspect of this invention is to provide cells which upon growth and differentiation produce *Brassica napus* L. var. pabularia (DC.) plants having the physiological and morphological characteristics of *Brassica napus* L. var. pabularia (DC.) cultivar KX-1.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. Means for preparing and maintaining plant tissue culture are well known in the art. By way of example, a tissue culture comprising organs has been used to produce regenerated plants. U.S. Patent Nos. 5,959,185, 5,973,234, and 5,977,445 describe certain techniques, the disclosures of which are incorporated herein by reference.

EXAMPLES

The foregoing examples of the related art and limitations related therewith are intended to be illustrative and not exclusive. Other limitations of the related art will become apparent to those of skill in the art upon a reading of the specification.

Example 1

Development of *Brassica napus* L. var. pabularia (DC.) cultivar KX-1

The *Brassica napus* L. var. pabularia (DC.) cultivar KX-1 is a dark purple *Brassica napus* L. var. pabularia (DC.) variety obtained after several rounds of crossing, self-pollination and selection.

Breeding History:

KX-1 was developed from a very unusual cross. KX-1 was previously thought to be a *Brassica oleracea* variety, but was later determined to be a *Brassica napus* variety through cytometry (e.g., it has the same DNA content as a *Brassica napus* plant).

The female parent is a proprietary plant of Applicant. The female plant is itself the result of the cross between a *Brassica napus* L. var. pabularia (DC.), (also generically known as Siberian Kale) with a *Brassica oleracea* var. acephala kale.

The male parent is a proprietary plant of Applicant. The male parent is itself the progeny of several complex crosses involving *Brassica napus* L. var. pabularia (DC.) and *Brassica oleracea* var alboglabra (also generically known as Kailan). This male plant was itself rather unexpected to obtain because of the incompatible blooming of the plants, as Siberian kale requires vernalization while kailan doesn't. Further, even after such crosses have been found possible by the present inventor, only very few seeds were produced, due to genetic incompatibility. The cross, between the female and male plants, that will lead to KX-1 took place in Gilroy, Calif. on Spring of the first year.

The resulting seed was grown in fall of the first year at Gilroy. Two selections were made and allowed to self, and the seed of each plant was collected individually. The two batches of seed were assigned the source codes B-1039-6-1 and, -2. The resulting seed was grown in fall of the second year at Gilroy. Nine selections were made from B-1039-6-2 of which three survived to produce seed. The seed were assigned the source code B-1158-23-1, -2 and -8. The resulting seed was grown in fall of year three at Gilroy. one selection was made and allowed to self, and the seed of the plant was collected and assigned the source code B-1242-119-1. The resulting seed was grown in fall of year four at Gilroy. One selection was made from the resulting plants and the seed of the plant was collected and assigned the source code B-1392-129-1. The resulting seed was grown in fall of year five at Gilroy. 127 plants were selected, their seeds collected in bulk and those seeds became KX-1.

Some of the criteria used to select the *Brassica napus* L. var. pabularia (DC.) cultivar KX-1 in various generations include: uniformity, color of the leaves, texture of the leaves, leaf thickness, shape, smoothness and seed production, length of hypocotyl and stem. It is worth to note that; to the best knowledge of the inventor, KX-1 is the first Siberian Kale having a Dark Purple color of the leaves.

KX-1 *Brassica napus* L. var. pabularia (DC.) cultivar is similar to the Red Russian variety sold for example by Johnny's Selected Seeds, but has numerous differences: KX-1 is purple with a green petiole while Red Russian is green with a slightly pink petiole, the texture of KX-1 is heavier and more succulent than Red Russian, KX-1 is more uniform. The leaf shape of KX-1 is similar to that of Red Russian but is more entire, with a greater leaf surface. Also, KX-1 produces seeds more readily and with less vernalization than Red Russian.

The *Brassica napus* L. var. pabularia (DC.) cultivar KX-1 has shown uniformity and stability for the traits, within the limits of environmental influence for the traits as described in the following Variety Descriptive Information. No variant traits have been observed or are expected for agronomically important traits in *Brassica napus* L. var. pabularia (DC.) cultivar KX-1.

*Brassica napus* L. var. pabularia (DC.) cultivar KX-1 has the following morphologic and other characteristics, (based primarily on data collected in California, all experiments done under the direct supervision of the applicant).

TABLE 1

| Variety Description Information | |
|---|---|
| Plant: | |
| *Brassica napus* L. var. *pabularia* (DC.) | |
| Seed: | |
| Color: | Black |
| Cotyledon to Fourth Leaf Stage: | |
| Shape of cotyledon: | Reniform |
| Shape of fourth leaf: | Ovate |
| Apical Margin: | Deeply pinnipartite |
| Basal Margin: | Deeply pinnipartite |
| Undulation: | Slight |
| Green Color: | Dark Purple |
| Anthocyanin Distribution: | Leaf blade |
| Anthocyanin Concentration: | Heavy |
| Rolling (curvature parallel to the spine of the leaf): | None |
| Cupping: | None |
| Reflexing (curvature perpendicular to the spine of the leaf): | Slight |
| Harvest-Mature Out Leaf, Head, Core: | |
| Margin Incision Depth: | Medium |
| Margin Indentation: | Deeply pinnipartite |
| Undulation of the Apical Margin: | Slight |
| Green Color: | Dark purple |
| Anthocyanin Distribution: | Leaf blade |
| Anthocyanin Concentration: | Heavy |
| Glossiness: | Moderate |
| Blistering: | Slight |
| Leaf Thickness: | Medium Thick |
| Trichomes: | Nearly Absent (Smooth) |
| Maturity (No. of Days of First Water date to Harvest): | NA |
| Outer Leaf Length (cm): full size harvest | 20.5 |
| Out Leaf Width (cm): full size harvest | 6.5 |
| Outer Leaf Length (cm): baby leaf size harvest | NA |
| Out Leaf Width (cm): baby leaf size harvest | NA |

Deposit Information

A deposit of the *Brassica napus* L. var. pabularia (DC.) seed of this invention is maintained by Shamrock Seed Company Inc., 3 Harris Place, Salinas, Calif. 93901-4593, USA. In addition, a sample of the *Brassica napus* L. var. pabularia (DC.) seed of this invention has been deposited with the National Collections of Industrial, Food and Marine Bacteria (NCIMB), 23 St Machar Drive, Aberdeen, Scotland, AB24 3RY, United Kingdom.

To satisfy the enablement requirements of 35 U.S.C. 112, and to certify that the deposit of the isolated strain of the present invention meets the criteria set forth in 37 C.F.R. 1.801-1.809, Applicants hereby make the following statements regarding the deposited *Brassica napus* L. var. pabularia (DC.) cultivar KX-1 (deposited as NCIMB Accession No. 42703):

1. During the pendency of this application, access to the invention will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 C.F.R. 1.807; and 5. The deposit will be replaced if it should ever become unavailable. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the NCIMB.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A seed of *Brassica napus* L. var. pabularia (DC.) designated KX-1, wherein a representative sample of seed of said *Brassica napus* L. var. pabularia (DC.) having been deposited under NCIMB No 42703.

2. A *Brassica napus* L. var. pabularia (DC.) plant, or a part thereof, or a plant cell thereof produced by growing the seed of claim 1.

3. The *Brassica napus* L. var. pabularia (DC.) part of claim 2, wherein the *Brassica napus* L. var. pabularia (DC.) part is selected from the group consisting of: a leaf, a flower, an ovule, a cell and pollen.

4. A *Brassica napus* L. var. pabularia (DC.) plant having all of the characteristics of *Brassica napus* L. var. pabularia (DC.) KX-1 listed in Table 1 when grown under the same environmental conditions, or a plant part or a plant cell thereof.

5. A *Brassica napus* L. var. pabularia (DC.) plant, or a plant part thereof, having all of the physiological and morphological characteristics of *Brassica napus* L. var. pabularia (DC.) KX-1, wherein a representative sample of seed of said *Brassica napus* L. var. pabularia (DC.) having been deposited under NCIMB No 42703.

6. A tissue culture of regenerable cells produced from the plant or plant part of claim 2, wherein a plant regenerated from the tissue culture has all of the characteristics of *Brassica napus* L. var. pabularia (DC.) KX-1 listed in Table 1 when grown under the same environmental conditions.

7. A *Brassica napus* L. var. pabularia (DC.) plant regenerated from the tissue culture of claim 6, said plant having all the characteristics of *Brassica napus* L. var. pabularia (DC.) KX-1, wherein a representative sample of seed of said *Brassica napus* L. var. pabularia (DC.) having been deposited under NCIMB No 42703.

8. A *Brassica napus* L. var. pabularia (DC.) leaf produced from the plant of claim 2.

9. A method for producing a *Brassica napus* L. var. pabularia (DC.) leaf comprising a) growing the *Brassica napus* L. var. pabularia (DC.) plant of claim 2 to produce a *Brassica napus* L. var. pabularia (DC.) leaf, and b) harvesting said *Brassica napus* L. var. pabularia (DC.) leaf.

10. A *Brassica napus* L. var. pabularia (DC.) leaf produced by the method of claim 9.

11. A method for producing a *Brassica* seed comprising crossing the *Brassica napus* L. var. pabularia (DC.) plant of claim 2 with itself or a second, distinct *Brassica* plant.

12. An F1 *Brassica* seed produced by the method of claim 11.

13. A method for producing a *Brassica napus* L. var. pabularia (DC.) seed comprising self-pollinating the *Brassica napus* L. var. pabularia (DC.) plant of claim 2 and harvesting the resultant *Brassica napus* L. var. pabularia (DC.) seed.

14. A *Brassica napus* L. var. pabularia (DC.) seed produced by the method of claim 13.

15. A method of producing a *Brassica* plant derived from the *Brassica napus* L. var. pabularia (DC.) KX-1, the method comprising (a) crossing the plant of claim 2 with a second *Brassica* plant to produce a progeny plant.

16. The method of claim 15 further comprising the step of:
(b) crossing the progeny plant derived from *Brassica napus* L. var. pabularia (DC.) KX-1 with itself or a second plant to produce a seed of progeny plant of subsequent generation;
(c) growing the progeny plant of the subsequent generation from the seed
(d) crossing the progeny plant of the subsequent generation with itself or a second plant, to produce a *Brassica* plant derived from the *Brassica napus* L. var. pabularia (DC.) KX-1.

17. The method of claim 16 further comprising the step of: (e) repeating steps (b) and/or (c) to produce a *Brassica* (DC.) plant derived from the *Brassica napus* L. var. pabularia (DC.) KX-1.

18. The plant of claim 2 comprising a single locus conversion and otherwise essentially all the characteristics of KX-1 listed in Table 1 when grown in the same environmental conditions.

19. The plant of claim 18 wherein the single locus conversion confers said plant with herbicide resistance.

20. The plant of claim 18 wherein the single locus conversion is an artificially mutated gene or nucleotide sequence.

21. The plant of claim 18 wherein the single locus conversion is a gene that has been modified through the use of new breeding techniques.

22. A method of introducing a desired trait into *Brassica napus* L. var. pabularia (DC.) KX-1 comprising:
(a) crossing a *Brassica napus* L. var. pabularia (DC.) KX-1 plant grown from *Brassica napus* L. var. pabularia (DC.) KX-1 seed, wherein a representative sample of seed has been deposited under NCIMB No. 42703, with another *Brassica* plant that comprises a desired trait to produce F1 progeny plants.

23. The method of claim 22, further comprising:
(b) selecting one or more progeny plants that have the desired trait to produce selected progeny plants;
(c) crossing the selected progeny plants with the *Brassica napus* L. var. pabularia (DC.) KX-1 plants to produce backcross progeny plants;
(d) selecting for backcross progeny plants that have the desired trait and all of the physiological and morphological characteristics of *Brassica napus* L. var. pabularia (DC.) KX-1 listed in Table 1 when grown in the same environmental conditions to produce selected backcross progeny plants; and
(e) repeating steps (c) and (d) three or more times in succession to produce selected fourth or higher backcross progeny plants that comprise the desired trait and all of the physiological and morphological characteristics of *Brassica napus* L. var. pabularia (DC.) KX-1 listed in Table 1 when grown in the same environmental conditions.

* * * * *